(12) United States Patent  (10) Patent No.: US 8,288,156 B2
Inami et al.  (45) Date of Patent: Oct. 16, 2012

(54) ANALYTICAL CHIP AND ANALYZER (75) Inventors: Hisao Inami, Matsudo (JP); Yasuhiko Sasaki, Chiyoda (JP); Ryo Miyake, Tsukuba (JP)

(73) Assignee: Hitachi, Ltd., Tokyo (JP)

( * ) Notice: Subject to any disclaimer, the term of this patent is extended or adjusted under 35 U.S.C. 154(b) by 635 days.

(21) Appl. No.: 11/858,571

(22) Filed: Sep. 20, 2007

(65) Prior Publication Data

US 2008/0014121 A1 Jan. 17, 2008

Related U.S. Application Data (63) Continuation of application No. 10/464,674, filed on Jun. 19, 2003, now abandoned.

(30) Foreign Application Priority Data

Jun. 21, 2002 (JP) ................................ 2002-180746

(51) Int. Cl.
C12M 1/36 (2006.01)
C12M 1/38 (2006.01)
C12M 3/00 (2006.01)
(52) U.S. Cl. ............... 435/288.5; 435/285.2; 435/6.1; 435/288.3; 435/288.4; 435/288.7; 435/287.3; 422/82.05; 422/500; 422/566
(58) Field of Classification Search ............. 435/285.2, 435/6.1, 288.3, 288.4, 288.5, 288.7, 287.3; 422/82.05, 500, 566
See application file for complete search history.

(56) References Cited

U.S. PATENT DOCUMENTS

| | | | |
|---|---|---|---|
| 6,235,471 B1 * | 5/2001 | Knapp et al. | 435/6.19 |
| 6,383,452 B1 | 5/2002 | Miyake et al. | |
| 6,645,758 B1 | 11/2003 | Schnipelsky et al. | |
| 6,660,517 B1 | 12/2003 | Wilding et al. | |
| 6,706,519 B1 | 3/2004 | Kellogg et al. | |
| 6,713,023 B2 | 3/2004 | Bass et al. | |
| 7,516,351 B2 | 4/2009 | Inami et al. | |
| 2002/0055167 A1 | 5/2002 | Pourahmadi et al. | |
| 2003/0008286 A1 * | 1/2003 | Zou et al. | 435/6 |

FOREIGN PATENT DOCUMENTS

| | | |
|---|---|---|
| EP | 0 594 259 A1 | 4/1994 |
| EP | 1 203 959 A1 | 5/2002 |
| JP | 06-197751 | 7/1994 |
| JP | 9-504732 | 3/1995 |
| JP | 2001-527220 | 7/1999 |
| JP | 2000-266759 | 9/2000 |
| JP | 2000-287682 A | 10/2000 |
| JP | 2001-004628 A | 1/2001 |
| JP | 2001-056337 A | 2/2001 |
| JP | 2002-318229 A | 10/2002 |
| JP | 2003-088367 A | 3/2003 |
| WO | WO 91/06678 A1 | 5/1991 |
| WO | WO 95/06870 A1 | 3/1995 |

(Continued)

*Primary Examiner* — Nathan Bowers
(74) *Attorney, Agent, or Firm* — Antonelli, Terry, Stout & Kraus, LLP.

(57) ABSTRACT

An analytical chip and analyzer are disclosed. The analytical chip comprises a substrate and reaction cells that are formed in the substrate for receiving a sample collected from a living body. A reagent storage portion is used to store reagents to be supplied to the reaction cells. Flow paths are provided to connect the reaction cells to the reagent storage portions, thereby allowing the reagents stored in the reagent storage portions to flow into the reaction cells.

3 Claims, 8 Drawing Sheets

FOREIGN PATENT DOCUMENTS

| | | |
|---|---|---|
| WO | WO 98/28440 | 7/1998 |
| WO | WO 98/52691 A1 | 11/1998 |
| WO | WO 98/53311 A2 | 11/1998 |
| WO | WO 99/33559 A1 | 7/1999 |
| WO | WO 02/23180 A1 | 3/2000 |
| WO | WO 00/36390 A2 | 6/2000 |
| WO | WO 00/62931 A1 | 10/2000 |
| WO | WO 00/67907 A2 | 11/2000 |
| WO | WO 00/72970 A1 | 12/2000 |
| WO | WO 00/78455 A1 | 12/2000 |
| WO | WO 01/13127 A1 | 2/2001 |
| WO | WO 02/10732 A1 | 2/2002 |

* cited by examiner

ANALYTICAL CHIP AND ANALYZER

CROSS-REFERENCE TO RELATED APPLICATION

This application is a Continuation application of application Ser. No. 10/464,674, filed Jun. 19, 2003 now abandoned, which claims priority from Japanese Patent Application No. 2002-180746, filed on Jun. 21, 2002, the contents of which are incorporated herein by reference in their entirety.

BACKGROUND OF THE INVENTION (1) Field of the Invention

The present invention relates to an analytical chip for subjecting a subject to analysis.

(2) Description of the Related Art

JP-A-2000-266759 discloses, as an analyzer usable for POC testing, an analyzer comprising a chip comprising an organic polymer flat plate having fine grooves for flow of fluids, respectively, on its surface, and a photothermic conversion detector for measuring a physical quantity change accompanying a partial temperature change of a liquid, by irradiating at least a portion of the liquid in the groove on the chip with exciting light. In this analyzer, at first, 200 μL of a sample is poured into a reservoir for sample and 200 μL of a reagent into a reservoir for reagent. Then, electro-osmosis flows from the aforesaid reservoir for sample and reservoir for reagent to a reservoir for waste liquid are caused to send the sample to the reservoir for waste liquid through a groove connecting the reservoir for sample to the reservoir for waste liquid and send the reagent to the reservoir for waste liquid through a groove connecting the reservoir for reagent to the reservoir for waste liquid. In this case, since the above-mentioned two kinds of the grooves meet each other on the upstream side of the reservoir for waste liquid, the reagent and the sample are mixed in the single groove formed by the meeting and the reaction goes to completion in 3 to 5 minutes. The sample after completion of the reaction is irradiated with laser beams, followed by detection by a photothermic conversion method.

JP-A-6-197751 discloses a magnifying detector for a nucleic acid sample containing reagents. JP-A-2001-527220 discloses a disposable cartridge containing reagents.

However, in the analyzer disclosed in the above reference, the reduction of the amount of the reagent supplied for the reaction is limited because the sample and the reagent react with each other while flowing in the grooves of the analytical chip. Moreover, the reaction time is not sufficiently reduced because the sample and the reagent are mixed while flowing.

Carrying out a rapid analysis is important in an analyzer used as follows: a sample is fed to a container (e.g. a substrate) in which reagents necessary for reaction have been previously stored, to be reacted with the reagents in the container, and the container is disposed of after the analysis. In addition, carrying out the analysis easily with high precision is required in such an analyzer.

The present invention provides an analytical chip in which reagents for reaction are previously stored and which can be disposed of together with the reagents after analysis, and an analyzer. The analytical chip and analyzer provided solve the above problems. The present invention provides, in particular, a disposable analytical chip that is easy to handle and permits rapid analysis, and an analyzer equipped with the analytical chip.

SUMMARY OF THE INVENTION

For the solution of the above problems, the analytical chip of the present invention may be a disposable analytical chip comprising a reaction cell(s) in which a sample is stored and the reaction of said sample with each of reagents individually introduced into the reaction cell(s) is allowed to proceed; one or more reagent storage portions for storing the reagents which are connected to said reaction cell; and a connecting tube(s) (a nozzle(s)) connecting said reaction cell to said reagent storage portion(s). The reaction cell(s) may be of either an open type or a closed type. The number of the reaction cell(s) may be either one or more.

Specifically, the analytical chip of the present invention may have the following structure.

(1) The analytical chip is formed so that the reaction of a sample with each reagent is carried out in a sample feed portion.

Specifically, the analytical chip is that characterized by comprising a substrate; a reaction cell(s) formed in said substrate, into which a sample collected from a living body is introduced; a reagent storage portion(s) in which reagents to be supplied to said reaction cell(s) are stored; and a reagent nozzle portion(s) constituting a flow path(s) which connects said reaction cell(s) to said reagent storage portion(s) and along which said reagents stored in said reagent storage portion(s) flow into said reaction cell(s).

When as described above, the reaction is carried out in the portion into which the sample is fed, the amounts of the reagents can be reduced as compared with the case where a reaction portion is formed downstream to a portion where each reagent is mixed with the sample. Furthermore, the reaction can be rapidly carried out. Therefore, the analytical chip is suitable as a disposal analytical chip.

(2) The analytical chip is that having a mechanism for controlled feed of a flow of each reagent by the use of an external fluid.

The analytical chip is, for example, that characterized by comprising a substrate; a reaction cell(s) formed in said substrate, into which a sample collected from a living body is introduced; a reagent storage portion(s) in which reagents to be supplied to said reaction cell(s) are stored; a reagent nozzle portion(s) constituting a flow path(s) which connects said reaction cell(s) to said reagent storage portion(s) and along which said reagents stored in said reagent storage portion(s) flow into said reaction cell(s); and a fluid-supplying path(s) which leads to said reagent storage portion(s) and supplies a fluid for allowing said reagents to flow from said reagent storage portion(s) to said reagent nozzle portion(s), to said reagent storage portion(s).

For example, said fluid-supplying path(s) is equipped with an introduction portion for introducing said fluid from the outside.

(3) The analytical chip is such that reagent storage portion(s) is connected to a reaction cell(s) by a fine flow path(s).

The analytical chip is, for example, that characterized by comprising a substrate; a reaction cell(s) formed in said substrate, into which a sample collected from a living body is introduced; a reagent storage portion(s) in which reagents to be supplied to said reaction cell(s) are stored; and a reagent nozzle portion(s) constituting a flow path(s) which connects said reaction cell(s) to said reagent storage portion(s) and along which said reagents stored in said reagent storage portion(s) flow into said reaction cell(s), wherein said flow path(s) is formed by the formation of a gap(s) extending from said reagent storage portion(s) to said reaction cell, at least before the introduction of said sample.

In particular, the fine flow path(s) preferably has a region where the sectional area of the flow path is 15,000 $\mu m^2$ or less.

(4) In any of the above items (1) to (3), the above-mentioned reagent storage portion(s) may have a region which is deformed by an external force so as to reduce the capacity of the reagent storage portion(s), in place of the above-mentioned mechanism for supplying a fluid from the outside.

(5) In any of the above items (1) to (4), the above-mentioned fluid-supplying path is characterized in that its connecting portion to said reagent storage portion is formed in a region present at a distance of 80% or more of the distance between the connecting portion of said reagent nozzle to said reagent storage portion and the farthest region of the inner wall of said reagent storage portion.

(6) In any of the above items (1) to (5), the above-mentioned substrate comprises a first substrate and a second substrate formed on one principal surface of the first substrate; the above-mentioned reagent storage portion(s) is formed as a region(s) for storing said reagents, between said first substrate and said second substrate; and at least a part of the above-mentioned reagent nozzle(s) is formed in a region(s) outside the region(s) where said reagent storage portion(s) is formed, in relation to the direction perpendicular to said principal surface.

(7) In any of the above items (1) to (6), the above-mentioned fluid-supplying path(s) is formed so as to have a capacity larger than that of the above-mentioned reagent nozzle(s).

(8) In any of the above items (1) to (7), the above-mentioned fluid-supplying path(s) is formed so as to have a minimum flow path sectional area larger than that of the above-mentioned reagent nozzle(s).

(9) In any of the above items (1) to (8), the above-mentioned reagent storage portions and the above-mentioned reagent nozzles connecting the reagent storage portions to the reaction cell(s) are provided in numbers, respectively, of two or more.

(10) In any of the above items (1) to (9), in at least the above-mentioned reaction cell(s), a reflective plate capable of reflecting light due to the reaction of the sample introduced into the reaction cell(s) with each reagent is set in the above-mentioned substrate.

(11) In any of the above items (1) to (10), the above-mentioned substrate comprises an organic material as its main constituent.

(12) In any of the above items (1) to (11), the flow paths connecting the reaction cell(s) and reagent storage portion(s) of the analytical chip are preferably similar in length as much as possible. For example, a plurality of said reagent storage portions are formed in said substrate and the shortest flow path among the flow paths from said reagent storage portions to said reaction cell(s) has a length of 95% or more of the length of the longest flow path. Owing to such lengths of the flow paths, the control of the feed rate of a liquid is facilitated, so that a chip can be provided which permits high-precision detection. The analytical chip is suitable, for example, in the case of causing a luminous or fluorescent reaction by the use of a reagent, such as the case of feeding a sample containing genetic information.

Alternatively, the analyzer of the present invention preferably comprises a member for supporting an analytical chip having at least any of the characteristics described above (this member preferably has a flow path(s) capable of leading to the flow path(s) of the analytical chip, and a groove for adsorption); a fixing mechanism for fixing the analytical chip to said supporting member so that the chip can be detached; a mechanism (a pump) for pushing out the reagents in the reagent storage portion(s) into the reaction cell(s) in the analytical chip by sending a fluid to the reagent storage portion(s) in the analytical chip through the flow path(s) of the substrate (i.e., the aforesaid supporting member) and the flow path(s) of the analytical chip; and a detection portion for detecting the reaction of the sample stored and each reagent introduced (the reaction may be detected by employing any of light emission, fluorescence emission and colorimetry).

(13) The analyzer is, for example, that comprising an analytical chip setting portion for setting therein an analytical chip comprising a reaction cell(s) into which a sample collected from a living body is introduced, a reagent storage portion(s) in which reagents to be supplied to said reaction cell(s) are stored, and a reagent nozzle portion(s) connecting said reaction cell(s) to said reagent storage portion(s); a supplying mechanism for supplying a fluid for discharging said reagents in said reagent storage portion(s) into said reagent nozzle portion(s), to the reagent storage portion(s) of said analytical chip; and a detection portion which faces said reaction cell(s) and detects light emitted in said reaction cell(s).

(14) In the above item (13), the analytical chip is preferably held by so-called vacuum chuck.

For example, said analytical chip setting portion is equipped with a fixing mechanism for fixing said analytical chip in said analytical chip setting portion. In addition, it is equipped with a path leading to a vacuum pump.

Owing to the analyzer of the present invention, it is possible to provide a small and portable apparatus that can give analysis results rapidly and is suitable as an analyzer used in a medical treatment site, such as an analyzer used in POC testing. Moreover, an apparatus easy to handle can be formed which is suitable for use in a routine examination carried out in a place near a patient, such as a clinic.

Furthermore, the analyzer is suitable also for a manner of use in which the chip is replaced with fresh chip and disposed of for each sample, because the amounts of the reagents used are slight.

The analytical method of the present invention preferably comprises a procedure of heating a reaction cell(s) accommodating a sample, by means of a temperature control mechanism to heat said sample to a certain temperature in a short time; a procedure of detecting light emission caused by the reaction of the sample with each of reagents supplied, in said reaction cell(s); and a procedure of cooling the reaction cell(s) to cool said sample to room temperature in a short time.

(15) The analytical method comprises a step of lowering the temperature and then raising the temperature, between steps of supplying a plurality of nucleotides, respectively.

Specifically, the analytical method is that characterized by comprising a first supplying step in which a first nucleotide is supplied to a sample containing a single-stranded DNA; a second supplying step in which a second nucleotide is supplied to said sample; a first heating step in which said first nucleotide and said sample are adjusted to a first temperature higher than room temperature; a step of lowering the temperature from said first temperature to a second temperature lower than said first temperature; and a step of adjusting said second nucleotide and said sample to a third temperature higher than said second temperature.

It is preferable to add a first detection step in which the interaction between said first nucleotide and said sample is detected, after said first supplying step. In addition, it is preferable to add a second detection step in which the interaction between said second nucleotide and said sample is detected, after said second supplying step.

Said sample may be a sample containing a single-stranded DNA having a primer bonded thereto. The above-mentioned nucleotides include nucleotides complementary to the bases constituting said DNA. Nucleotides of A, T, G and C are preferably supplied in order. The above-mentioned first or third temperature is preferably 45° C. or lower. As said temperature, a temperature of 25° C. or higher is effective.

(16) A method for using an analytical chip, characterized by comprising a step of providing an analytical chip comprising a reaction cell(s) into which a sample collected from a living body is introduced, a reagent storage portion(s) in which reagents to be supplied to said reaction cell(s) have been stored, and a reagent nozzle portion(s) constituting a flow path(s) which connects said reaction cell(s) to said reagent storage portion(s) and along which said reagents stored in said reagent storage portion(s) flow into said reaction cell(s); a step of solidifying the reagents in said reagent storage portion(s) of said analytical chip provided, by cooling; a step of conveying said analytical chip in which said reagents solidified have been stored; a step of heating said analytical chip conveyed, to melt said reagents; a step of introducing the sample collected from a living body, into said reaction cell(s) to mix the same with each of said reagents; and a step of detecting the reaction caused by this mixing.

According to this method, the deterioration of the reagents can be suppressed and damage to the analytical chip and the flow of the stored reagents can be reduced even when an external force is applied during handling (e.g. conveyance) of the analytical chip. In addition, since an analytical chip can be provided which permits easy and high-precision analysis, highly reliable analysis can be carried out. Even in the case of reagents that are rapidly inactivated, such as many reagents for biochemical analysis, analysis can be carried out while keeping the reagents highly active. Moreover, as compared with the case where a user dispenses the reagents into reagent reservoirs from reagent tanks just before examination in order to prevent the inactivation of the reagents, the burden of the dispensation on the user and the possibility of contamination of the reagents can be easily reduced.

For example, in the analytical chip, said flow path preferably has such a shape that a gap extending from said reagent storage portion to said reaction cell is formed, at least before the introduction of said sample.

(17) As to handling of the analytical chip, a method for using an analytical chip is preferably adopted which is characterized by comprising a step of providing an analytical chip comprising a reaction cell(s) into which a sample collected from a living body is introduced, a reagent storage portion(s) in which reagents to be supplied to said reaction cell(s) have been stored, and a reagent nozzle portion(s) constituting a flow path(s) which connects said reaction cell(s) to said reagent storage portion (s) and along which said reagents stored in said reagent storage portion(s) flow into said reaction cell(s); a step of solidifying the reagents in said reagent storage portion(s) of said analytical chip provided, by cooling; and a step of conveying said analytical chip in which said reagents solidified have been stored.

(18) A method for using an analytical chip may also be adopted which is characterized in the same manner as in the above item (16) except for comprising a step of introducing the provided analytical chip into a cooling unit to cool the same to a temperature higher than a temperature at which the reagents in said reagent storage portion(s) of said analytical chip are solidified, instead of solidifying the reagents; a step of conveying said analytical chip at a temperature which is lower than the temperature outside said cooling unit and is higher than a temperature at which said reagents are solidified; a step of heating said analytical chip conveyed; a step of introducing a sample collected from a living body, into said reaction cell(s) to mix the same with each of said reagents; and a step of detecting the reaction caused by this mixing.

Owing to this characteristic, the lowering of activity of the reagents can be suppressed, so that high-precision and efficient analysis can be carried out by the use of the analytical chip containing such reagents stored therein. Particularly when the reagents include an enzyme, the lowering of activity of the enzyme can be suppressed by cooling. In addition, it is possible to suppress a lowering of the activity caused by, for example, a pH change due to contact with, for instance, a cleaning fluid which adheres to a dispensing unit in dispensation with the dispensing unit during examination, by heating the analytical chip containing the reagents previously stored therein, and mixing the sample with each of said reagents in the analytical chip.

In particular, such a method is preferable to the method involving the solidification because the deformation of the above-mentioned flow path(s) by cubical expansion at the time of solidification can be prevented because the former method involves a step in which the reagents in a liquid state are kept in cold storage. For example, the temperature at the above-mentioned cooling can be adjusted to a temperature of not higher than about 10° C. and higher than a temperature at which the reagents are solidified.

For example, in the analytical chip, said flow path preferably has such a shape that a gap extending from said reagent storage portion to said reaction cell is formed, at least before the introduction of said sample.

(19) As to handling of the analytical chip, a method for using an analytical chip can be adopted which is characterized by comprising a step of providing an analytical chip comprising a reaction cell(s) into which a sample collected from a living body is introduced, a reagent storage portion(s) in which reagents to be supplied to said reaction cell(s) have been stored, and a reagent nozzle portion(s) constituting a flow path(s) which connects said reaction cell(s) to said reagent storage portion (s) and along which said reagents stored in said reagent storage portion(s) flow into said reaction cell(s); a step of introducing said analytical chip provided, into a cooling unit to cool the reagents in said reagent storage portion(s) to a temperature higher than the solidifying points of said reagents; and a step of conveying said analytical chip at a temperature which is lower than the temperature outside said cooling unit and is higher than a temperature at which said reagents are solidified.

(20) An information management center having a database concerning genetic information which is connected through a network to a plurality of users who carry out an analysis on the genes of a sample, said information management center being characterized by receiving information on the results of said analysis and the ID of each of said users from the user, transmitting evaluation informa-tion obtained by evaluating the thus received analysis result information on the basis of corresponding information in said database, to the user, and incorporating said analysis result information transmitted from the user into said database through the network connecting the user and said information management center to each other. Transmitting equipment may be installed for the above transmission. Receiving equipment may be installed for the reception. Controlling equipment may be installed for the incorporation.

(21) In the above item (20), said information management center receives information on use of an apparatus for the above analysis, and transmits this use information to a service provider which utilizes said use information and is connected to the information management center through a network. Said information management center receives information on information in the database from said service provider.

(22) In at least one of the above items (20) and (21), the service provider receives information on use of an apparatus for the above analysis from said information management center, and transmits information on information in the database to said service provider.

By using the analytical chip, analyzer and the like described above, there can be suitably carried out so-called POC (Point-of-Care) testing, such as home or bedside examination, or rapid examination in a place near a patient, such as a common clinic.

Specifically, a small and portable analyzer that requires an analysis time shorter than before can be provided, for example, by combining the above-mentioned analytical chip having a very small reaction cell(s) with a simple photodetector. Optimum circumstances for POC examination can be created by providing a user with a disposable analytical chip in which reagents have been previously stored in amounts required for only one run of examination and which is in a frozen state. Suitable medical services utilizing genetic information and clinical data can be provided by making preparations for examination services for POC by using the analytical chip of the present invention as an essential.

The present invention makes it possible to provide an analytical chip which is easy to handle, permits rapid analysis, permits previous storage of reagents for reaction therein, and can be disposed of together with the reagents after analysis, and an analyzer equipped with the analytical chip.

Other objects, features and advantages of the invention will become apparent from the following description of the embodiments of the invention taken in conjunction with the accompanying drawings.

DESCRIPTION OF REFERENCE NUMERALS

100—substrate, 101-1, 101-2, 101-3 and 101-4—pumps, 102-1, 102-2, 102-3 and 102-4—flow paths of substrate, 103—temperature control mechanism, 104—adsorption groove, 105—pump for vacuum exhaustion, 106—base plate of analytical chip, 110—analytical chip, 111-1—dATP vessel, 111-2—dCTP vessel, 111-3—dTTP vessel, 111-4—dGTP vessel, 112-1, 112-2, 112-3 and 112-4—flow paths of analytical chip, 113—reaction cell, 114-1—dATP nozzle, 114-2—dCTP nozzle, 114-3—dTTP nozzle, 114-4—dGTP nozzle, 115—PDMS first layer, 116—PDMS second layer, 120—photodetector, 121—electric source, 122—recorder, 131—suction opening, 132—discharge opening, 133—diaphragm, 134—pump chamber, 135—suction valve, 136—discharge valve, 137—actuator, 207—photosensitive thick-film resist, 208—silicon wafer, 209—photomask, 210—PDMS, 301—DNA sample, 302—single-stranded DNA sample, 303—primer, 310—mixed reagent, 311—dATP, 312—dCTP, 313—dTTP, 314—dGTP, 400—analytical chip, 401—reaction cell, 402-1, 402-2, 402-3 and 402-4—reagent vessels, 403-1, 403-2, 403-3 and 403-4—reagent nozzles, 404-1, 404-2, 404-3 and 404-4—actuators, 405—PDMS first layer, 406—PDMS second layer, 500—service provider, 501—user, 502—information management center, 503—analyzer, 504—analytical chip, 505—internet, 506—examination data, 507—diagnosis information, 508—database, 509—consumption information.

PREFERRED EMBODIMENT OF THE INVENTION

Examples of analysis of the base sequence of DNA are explained below as examples of the present invention.

Example 1

Principle of the Analysis

PCTWO No. 98/28440 discloses a method for analyzing the base sequence beyond a primer of a DNA sample having the primer bonded thereto, as a method for analyzing the base sequence of DNA. Specifically, four kinds of deoxynucleotide triphosphates (dNTPs), i.e., deoxythymine triphosphate (dTTP), deoxyguanidine triphosphate (dGTP), deoxycytosine triphosphate (dCTP) and deoxyadenine triphosphate (dATP) which have complementarity (i.e., attraction between bases A and T or between bases C and G by hydrogen bonding) to four bases constituting the DNA sample, i.e., adenine (A), cytosine (C), guanine (G) and thymine (T), respectively, are added to the DNA sample in regular order. When the dNTP added is bonded to the DNA sample, pyrophosphate is produced as a by-product. Therefore, this pyrophosphate is detected by a luminous reaction. The base sequence of the DNA sample can be determined by adding the four kinds of dNTPs in regular order to know which dNTP causes light emission when added. The reaction procedure described above is broadly divided into the following three stages.

First Stage

When the dNTP added is bonded to the DNA sample in the presence of DNA polymerase (DNA synthetase), the primer is extended and pyrophosphate (PPi) is liberated from the dNTP.

$$(DNA)_n + dNTP \rightarrow (DNA)_{n+1} + Ppi \qquad (1)$$

Second Stage

PPi reacts with adenosine 5'-phosphosulfate (APS) in the presence of adenosine triphosphate sulfurylase (ATP sulfurylase) to be converted to adenosine triphosphate (ATP).

$$PPi + APS \rightarrow ATP + SO_4^{2-} \qquad (2)$$

Third Stage

The ATP produced reacts with luciferin in the presence of luciferase to produce oxyluciferin, a luminous substance. The extension of the primer is analyzed by detecting light emitted by the oxyluciferin. That is, whether the dNTP added and the DNA sample are combined or not is judged.

$$ATP + luciferin + O_2 \rightarrow AMP + PPi + oxyluciferin + CO_2 + light \tag{3}$$

The unreacted dNTP and the excess ATP are decomposed by nucleases such as apyrase.

$$dNTP \rightarrow dNDP + PPi \rightarrow dNMP + PPi \tag{4}$$

$$ATP \rightarrow ADP + PPi \rightarrow AMP + PPi \tag{5}$$

(Structure of an Analyzer)

Figure 1:
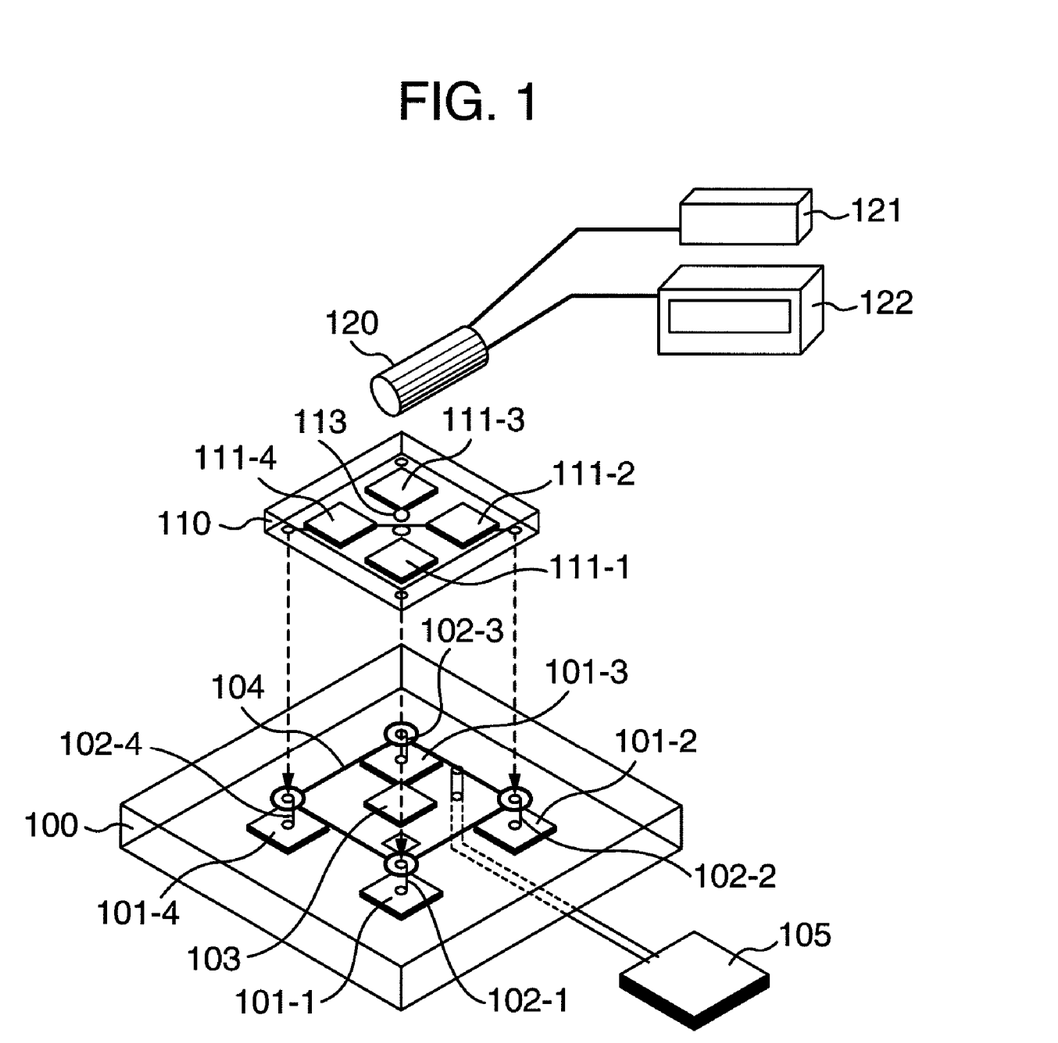
FIG. 1 is a perspective view showing one example of the structure of the apparatus described in Example 1.
Figure 2:
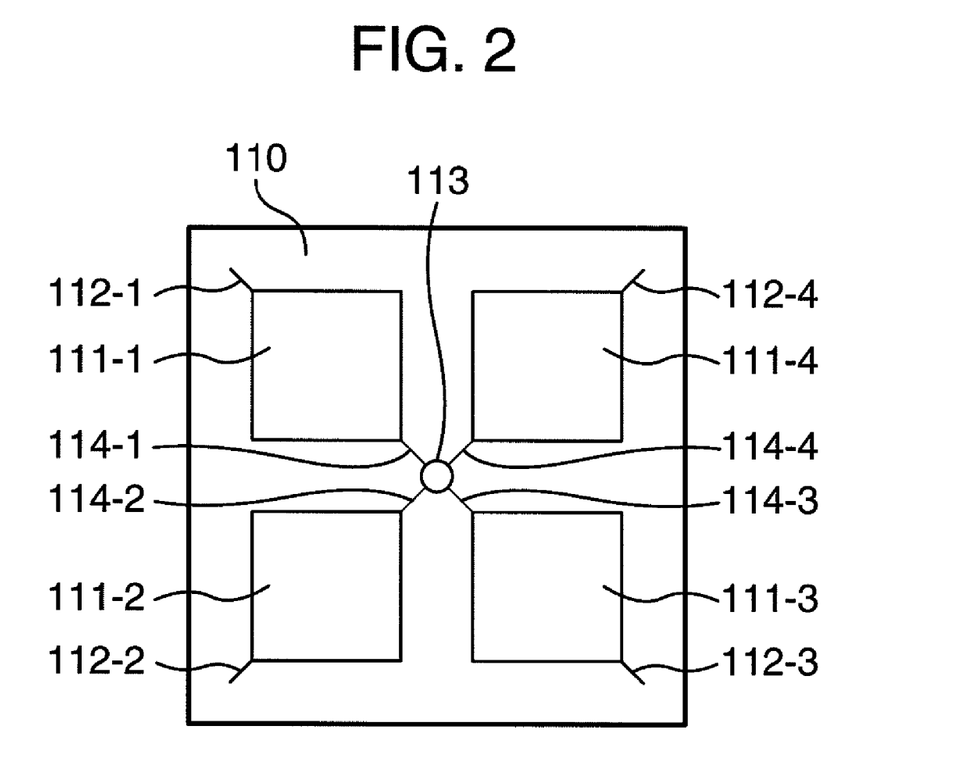
FIG. 2 is an enlarged view showing the structure of the analytical chip shown in FIG. 1.
Figure 3:
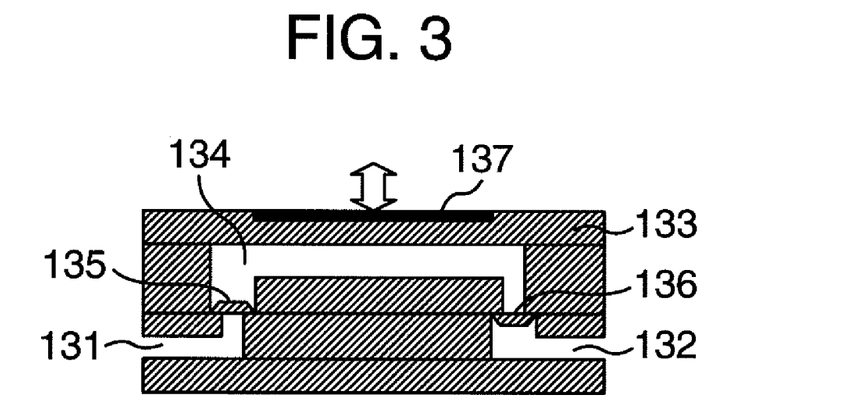
FIG. 3 is a cross-sectional view showing the structure of the pump shown in FIG. 1.

The structure of an analyzer is explained with reference to FIG. 1, FIG. 2 and FIG. 3. FIG. 1 is a perspective view of the analyzer. FIG. 2 is a detail view of an analytical chip. FIG. 3 is a cross-sectional view of a pump.

The analyzer is composed of three constituents, i.e., a substrate 100, an analytical chip 110 and a photodetector 120 when broadly divided. The substrate 100 comprises four pumps 101-$i$ ($i$=1, 2, 3 or 4) for sending a slight volume of a fluid (the volume of the fluid sent per sending operation is 0.1 μL in the present example), four flow paths of substrate 102-$i$ ($i$=1, 2, 3 or 4) along which the fluid discharged from the pumps flows, a temperature control mechanism 103 for optimizing the temperature of the analytical chip 110 which is formed in a region corresponding to a region where the reaction cell 113 of the analytical chip 110 is located, and an adsorption groove 104 for adsorbing the analytical chip 110. In the present example, the numbers of the pumps 101-$i$ and the flow paths of substrate 102-$i$ are 4 because four kinds of dNTPs (dATP, dTTP, dGTP and dCTP) are used in the present example, though these numbers may be changed depending on purpose of the analysis.

When Pertier effect is utilized in the temperature control mechanism 103, either heating or cooling of the analytical chip 110 can easily be conducted merely by changing the direction of an electric current applied.

The shape of the pumps 101-$i$ is not particularly limited. In the present example, the pumps are silicone-made positive displacement pumps of about 1.5 mm in thickness as shown in FIG. 3. In each of the pumps, a suction opening 131, a discharge opening 132, a diaphragm 133, a pump chamber 134, a suction valve 135 and a discharge valve 136 are formed by micro-fabrication. The pumps are driven by deforming the diaphragm 133 by the use of an external actuator 137. That is, when the diaphragm 133 is swollen upward, the pressure inside the pump chamber 134 is reduced. Therefore, the discharge valve 136 is closed and the suction valve 135 is opened, so that a liquid is sucked into the pump chamber 134 through the suction opening 131. When the diaphragm 133 is then depressed downward, the pressure inside the pump chamber 134 is increased. Therefore, the suction valve 135 is closed and the discharge valve 136 is opened, so that the liquid is discharged from the pump chamber 134 through the discharge opening 132.

The analytical chip 110 to be placed on the substrate 100 has four dNTP vessels 111-$i$ ($i$=1, 2, 3 or 4) for storing therein four kinds of dNTPs (dATP, dTTP, dGTP and dCTP), respectively, i.e., a dATP vessel 111-1, a dCTP vessel 111-2, a dTTP vessel 111-3 and a dGTP vessel 111-4, and four flow paths of analytical chip 112-$i$ ($i$=1, 2, 3 or 4) for conducting the liquid sent through the flow paths of the substrate 100 to the dNTP vessels 111-$i$, respectively. The analytical chip 110 comprises regions to be connected to the flow paths of substrate 102-$i$, a reaction cell 113, and four dNTP nozzles 114-$i$ ($i$=1, 2, 3 or 4) connecting the reaction cell 113 to the four dNTP vessels 111-$i$, i.e., a dATP nozzle 114-1, a dCTP nozzle 114-2, a dTTP nozzle 114-3 and a dGTP nozzle 114-4. As described above, the numbers of the flow paths of analytical chip 112-$i$, the dNTP vessels 111-$i$, the dNTP nozzles 114-$i$ and the reaction cell 113 may be changed depending on purpose of the analysis. Said dNTP nozzles are preferably similar to one another in length. For example, the shortest nozzle among the dNTP nozzles preferably has a length of 95% or more of the length of the longest nozzle. Owing to such lengths of the dNTP nozzles, the control of the feed rate of the liquid is facilitated, so that the analysis can be carried out with high precision.

The analytical chip 110 is placed on the substrate 100 and the substrate 100 is fixed. The flow paths of analytical chip 112-$i$ are connected to the flow paths of substrate 102-$i$. Specifically, the analytical chip 110 can be adsorbed on the substrate 100 by evacuating the adsorption groove 104 of the substrate 100 with a pump for vacuum exhaustion 105. By thus carrying out vacuum chuck, the flow paths of substrate 102-$i$ and the flow paths of analytical chip 112-$i$ are certainly connected together to prevent the leakage of the liquid, and the analytical chip 110 is made easily detachable from the substrate 100. For making the analytical chip 110 disposable in its use in POC, a method for fixing the analytical chip 110 by vacuum chuck is very practical.

The photodetector 120 is located so that the light-receiving surface of the photodetector 120 faces the reaction cell 113 (for example, the photodetector 120 is located over the reaction cell 113). As the photodetector 120, a CCD camera, a photomultiplier tube, a photodiode and the like can be used. The photodiode is preferable for miniaturizing the apparatus.

In the embodiment of the present invention, a small portable analyzer can be provided by placing the analytical chip 110 on the substrate 100 and combining the simple photodetector 120 with them, without using a large laser for excitation.

(Production of the Analytical Chip)

As a material for the analytical chip 110, a resin excellent in discardability is preferable to glass that entails high processing costs and is brittle. Although the kind of the resin is not particularly limited, a poly(dimethylsiloxane) (PDMS) (Silpot 184, mfd. by Dow Corning Asia Inc.) having the following excellent characteristics was used in the present example.

Good biocompatibility (conventional silicone rubber is physiologically inactive).

A pattern can be transferred with a precision of submicron (PDMS has a low viscosity and a high fluidity before curing and hence infiltrates small parts of complicated shape satisfactorily).

Low cost (PDMS is more inexpensive than pyrex, a material for micro-device).

Easily discardable by incineration.

Figure 4:
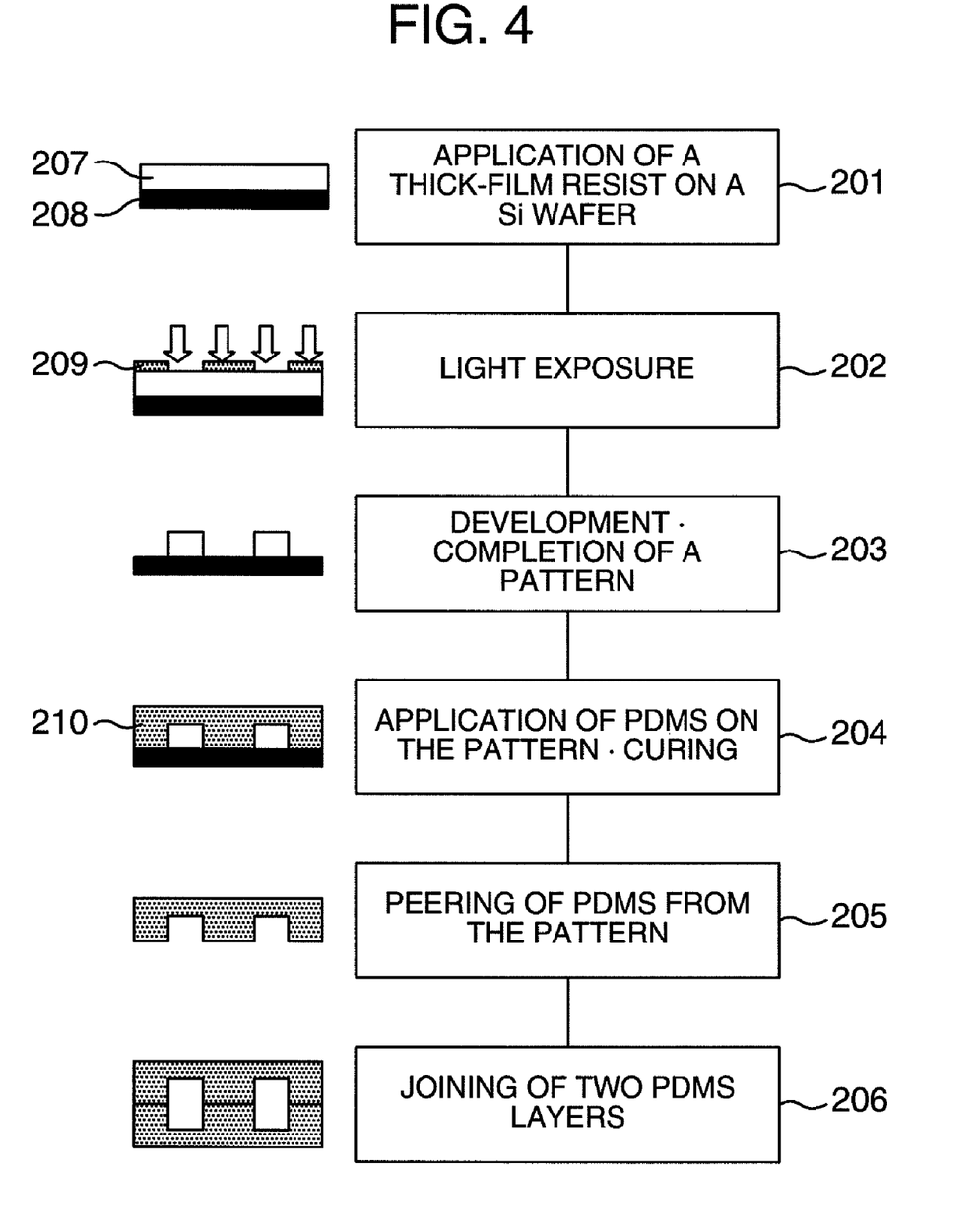
FIG. 4 is a flow chart showing a procedure for producing the analytical chip shown in FIG. 1.

FIG. 4 shows steps for the production of the analytical chip 110 by the use of a resin substrate (the case of using PDMS is described below as an example). The analytical chip can be shaped by forming a pattern in conformity with the constituents of the analytical chip by photolithography, and transferring the pattern to a resin.

When broadly divided, a process of the production comprises

[1] formation of each pattern to be transferred to PDMS, [2] transfer of the pattern to PDMS, and [3] joining of the resulting PDMS layers to each other.

[1] Formation of each pattern to be transferred to PDMS

A micro-pattern is formed through the following steps: a step of applying a photosensitive thick-film resist 207

(NANOSU-8, mfd. by Micro. Chem. Inc.) as a material for pattern on a silicon wafer 208 (step 201), a step of placing a photomask 209 on the photosensitive thick-film resist 207, followed by light exposure (step 202), and a step of development (step 3). A process for the formation is not limited to the above process. The above process is advantageous in that a curvilinear shape can be formed while maintaining a rectangular section, by photofabrication by wet etching.

[2] Transfer of the pattern to PDMS

PDMS 210 is applied on the pattern and heated to be cured (step 204). A PDMS layer 210 having a depressed pattern is obtained by the use of the raised micro-pattern (step 205).

[3] Joining of the PDMS layers to each other

Figure 5:
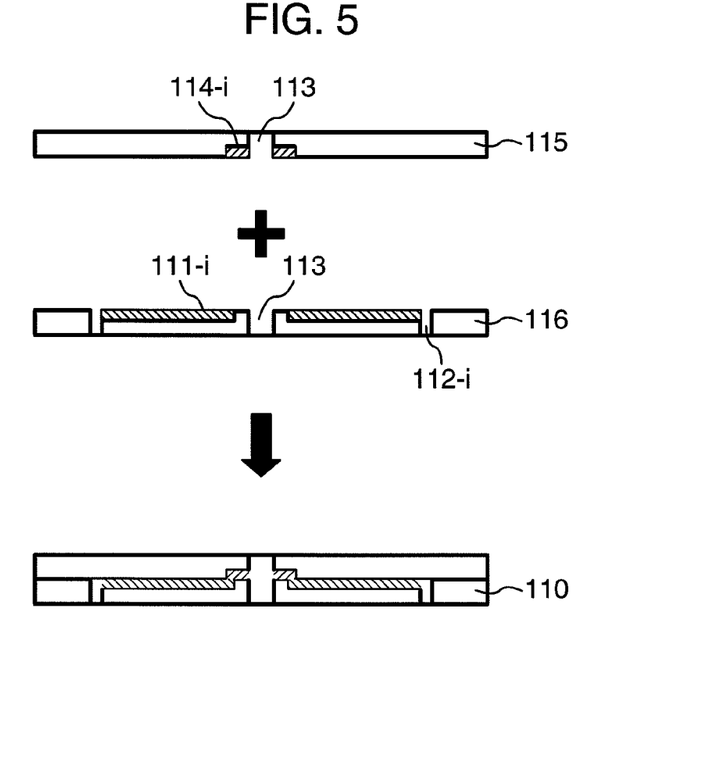
FIG. 5 is a cross-sectional view showing the structure of the analytical chip shown in FIG. 1.

The surfaces of the thus obtained PDMS layers 210 having the patterns, respectively, transferred thereto are subjected to oxygen plasma treatment, and the two PDMS layers 210 are placed one upon another to be joined together. The strength of joining is so sufficient that the PDMS layers 210 are broken when joining portions are tried to be peeled. The PDMS layer may be joined to a silicon plate or a glass plate. FIG. 5 shows a section of the analytical chip 110 obtained by the above process. As shown in FIG. 5, the analytical chip 110 is a joined product of a PDMS first layer 115 (25 mm long, 25 mm wide and 1 mm thick) having the dNTP nozzles 114-$i$ and reaction cell 113 formed thereon according to a pattern, and a PDMS second layer 116 (25 mm long, 25 mm wide and 1 mm thick) having the dNTP vessels 111-$i$, flow paths of analytical chip 112-$i$ and reaction cell 113 formed thereon according to another pattern. Needless to say, the analytical chip 110 can be produced by joining a PDMS layer having the flow paths of analytical chip 112-$i$, dNTP vessels 111-$i$, dNTP nozzles 114-$i$ and reaction cell 113 formed thereon according to a pattern to a flat PDMS plate having nothing formed thereon according to a pattern.

Figure 6:
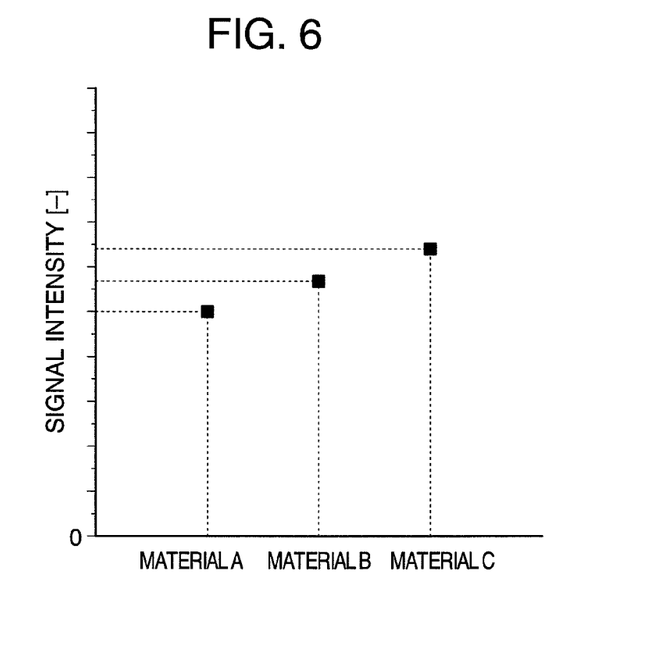
FIG. 6 is a graph showing the relationship between a material for the base plate of an analytical chip and the amount of emitted light detected.

When the reaction cell 113 formed by the above method is a through-hole, a plate as base is necessary. As described above, the base plate of the analytical chip 110 is preferably a material with a high thermal conductivity because it serves also as a medium capable of conducting heat from the temperature control mechanism 103 to the reaction cell 113. In addition, when the surface of the base plate is specular, emitted light due to a reagent in the reaction cell 113 is reflected from the base plate, so that the light emission intensity detected by the photodetector 120 over the reaction cell 113 is increased. FIG. 6 shows the results of carrying out the luminous reaction of ATP with luciferin in the presence of luciferase (formula (3)), a final and typical reaction in DNA analysis, after attaching each of three kinds of materials, i.e., material A, material B and material C which are different in reflectance, as the base plate of the analytical chip 110 to the bottom of the analytical chip 110. When a slice of silicon wafer was used as material C, the amount of light emitted was considerably larger than that attained when material A (glass) was used, owing to the effect of reflection by the specular surface of the slice. Therefore, a slice of silicon wafer which was good in thermal conductivity and can easily be joined to PDMS merely by oxygen plasma treatment was attached as the base plate of the analytical chip 110. For example, the above-mentioned base plate or the bottom of the reaction cell 113 is formed so as to have a reflectance higher than that of the surface of the aforesaid analytical chip.

A method for shaping PDMS is not limited to the above method. PDMS may be processed also by, for example, extrusion.

The dimensions of the constituents of the analytical chip 110 are as follows. The dNTP vessels 111-$i$ have a length of 10 mm, a width of 10 mm, a depth of 0.1 mm and a capacity of 10 μL. The shape of the dNTP vessels 111-$i$ is not particularly limited.

The flow paths of analytical chip 112-$i$ have a shape of section with a length of 1 mm and a width of 0.1 mm, and a length of 2 mm and lead to the dNTP vessels 111-$i$, respectively. The ends of the flow paths of analytical chip 112-$i$ are preferably formed near regions farthest from the edge faces of the dNTP nozzles 114-$i$, respectively. The ends are formed in regions present at a distance of 80% or more of the distance to the farthest positions, respectively, in the dNTP vessels 111-$i$, respectively. The formation in such a manner is preferable because it permits smooth flow and effective use of a liquid. The dNTP nozzles 114-$i$ have a shape of section with a length of 40 μm and a width 20 μm, and a length of 4 mm. The leakage of reagents into the reaction cell 113 from the dNTP vessels 111-$i$ can be effectively prevented by adjusting the sectional area of the dNTP nozzles 114-$i$ to a sufficiently low value of 1,000 μm$^2$ or less. The sectional area of the dNTP nozzles 114-$i$ is more preferably adjusted to 800 μm$^2$ or less, still more preferably 500 μm$^2$ or less. By thus reducing the sectional area of the dNTP nozzles 114-$i$ sufficiently, a simple structure can be formed without using a valve for handling a liquid. As to the lower limit of the sectional area, the dNTP nozzles 114-$i$ preferably have a sectional area of 80 μm$^2$ or more for the prevention of pulsation during the supply of a liquid. Alternatively, the dNTP nozzles 114-$i$ preferably have a sectional area of 300 μm$^2$ or more for the prevention of swelling of air bubbles in the liquid which hinders sending of the liquid. Considering the conveyance of the analytical chip in a frozen state, the dNTP nozzles 114-$i$ preferably have a sectional area of 300 μm$^2$ or more for the prevention of, for example, damage to the analytical chip. On the other hand, as to the upper limit of the sectional area, the dNTP nozzles 114-$i$ have a sectional area of 15,000 μm$^2$ or less so that the liquid can be properly held without a valve. The above-mentioned values were calculated according to the equation Pw=Pa+mg/R=γ(2/R) wherein Pw: liquid pressure, Pa: air pressure, mg/R: the pressure of a drop of water, γ: surface tension between the liquid and air, and R: the radius of the flow path. Considering the influence of a change in the volume of the analytical chip caused by the conveyance of the analytical chip in a frozen state, the sectional area is preferably 8,000 μm$^2$ or less. Considering the application of an external force during the conveyance, the sectional area is preferably 3,000 μm$^2$ or less. As to the shape of the flow paths, the upper limit or the lower limit is preferably chosen depending on the purpose from the above point of view.

For example, the reaction cell 113 connected to a plurality of the dNTP vessels 111-$i$ by the dNTP nozzles 114-$i$, respectively, has a diameter of 2 mm and a capacity of about 5 μL. The adjustment of the capacity of the reaction cell 113 to a very low value of 1 to 5 μL improves the thermal response and permits rapid control of temperature of the reaction cell 113. Thus, the reaction can be allowed to proceed under optimum conditions while varying the temperature of the reaction cell 113 at intervals of one or more seconds. Moreover, owing to the adjustment of the capacity of the reaction cell 113 to a very low value, each dNTP introduced into the reaction cell 113 from the dNTP vessel 111-$i$ is diffused throughout the reaction cell 113 in a short time (for example, about 1 second), resulting in an easy mixing operation. For simplification, employment of no mixing operation is thought of. In prior art (JP-A-2000-266759), the reaction is detected in 3 to 5 minutes while mixing a sample with a reagent in a flow path. On the other hand, the reaction can be detected in about 1 second by batchwise mixing of a sample with a reagent in the reaction cell 113 having a very small capacity of 1 to 5 μL. Adjusting the capacity of the reaction cell 113 to 1 to 7 μL is also effective. Also when the capacity is set to 1 to 10 μL, the adjustment to such a very small value is effective
(Procedure for the Analysis)

Figure 7:
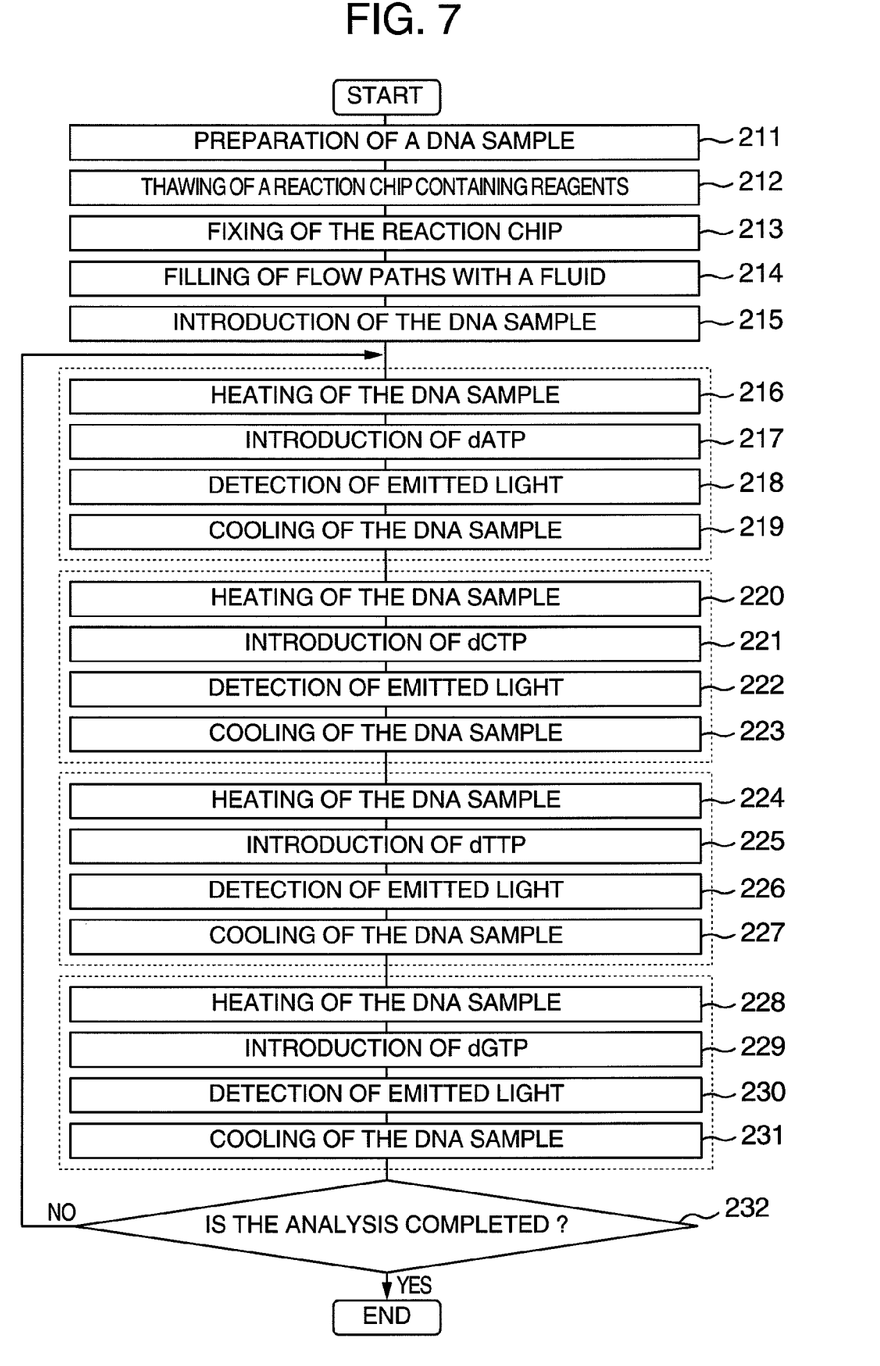
FIG. 7 is a flow chart showing a procedure for the analysis described in Example 1.
Figure 8:
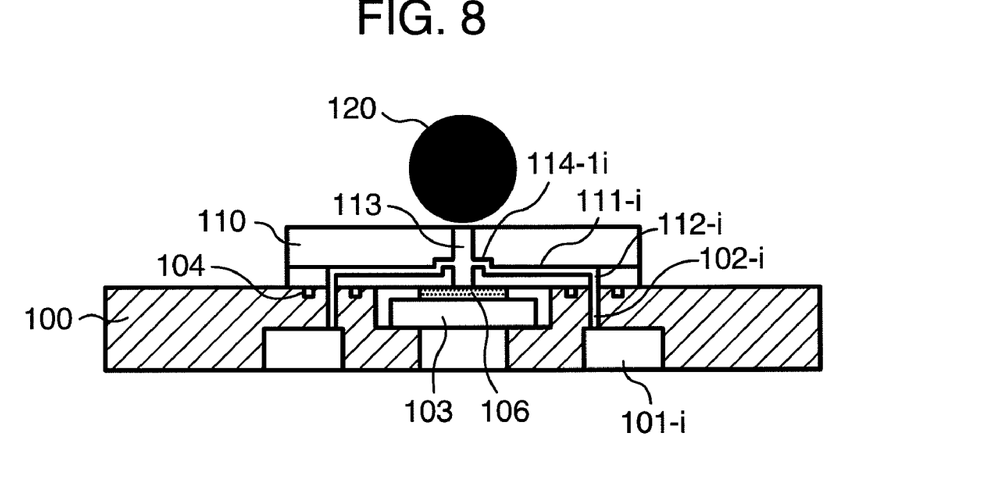
FIG. 8 is a cross-sectional view showing the structure of the apparatus described in Example 1.

A procedure for the analysis using the analytical chip 110 is explained below with reference to FIG. 7 and FIG. 8. FIG. 7 is a flow chart showing the procedure for the analysis. FIG. 8 is a cross-sectional view of the analyzer.

At first, a DNA sample is prepared. A primer having 15 to 20 bases is added to a single-stranded DNA sample whose base sequence is desired to be analyzed, followed by annealing at 95° C. for 5 minutes and then standing at room temperature for 30 minutes. Thus, the single-stranded DNA sample and the primer are combined. In this case, the unbound primer is washed away. Then, a reagent is prepared by mixing a primer-extending enzyme with a dNTP—decomposing reagent. As the primer-extending enzyme, Taq DNA polymerase, Tth DNA polymerase, Vent DNA polymerase or Thermosequenase may be used. As the dNTP-decomposing reagent, ATP diphosphatase or ATP pyrophosphatase may be used. A buffer solution is preferably added to the mixed reagent for the smooth progress of extension of the primer. As the buffer solution, for example, Tris-hydrochloric acid as pH buffer solution is preferably used after mixing with $MgCl_2$ for forming a complex (dNTP and $Mg^{2+}$) as a substrate for the extension reaction of the primer, and dithiothreitol for protecting the enzyme protein against oxidative denaturation (step 211).

After completion of the preparation of the DNA sample, the analytical chip 110 which has four kinds of dNTPs previously stored in the four dNTP vessels 111-i, respectively, and has been preserved in a frozen state, is thawed at room temperature. When the analytical chip 110 is provided for a user after previous storage therein of the dNTPs in amounts required for only one run of examination, these reagents are not wasted, resulting in an increased economical benefit, even if the analytical chip 110 is disposed of after the one run of the examination. Moreover, the analytical chip 110 saves the user the trouble of dispensing the dNTPs into the dNTP vessels 111-i, respectively, resulting in not only time reduction but also the prevention of contamination. In addition, when the analytical chip 110 is provided in a frozen state for the user and the user preserves the analytical chip 110 in a frozen state at 0° C., the activity of the dNTPs can be maintained for half a month. When the analytical chip 110 is preserved in a frozen state at –20° C., the activity of the dNTPs can be maintained for half a year or more. Optimum circumstances for POC examination can be created by thus storing the reagents in amounts required for only one run of examination in the disposable analytical chip 110 previously and providing the analytical chip 110 in a frozen state for the user (step 212).

Next, the analytical chip 110 is placed on the substrate 100 and it is confirmed that the flow paths of analytical chip 112-i and the flow paths of substrate 102-i, respectively, communicate with each other. Thereafter, the adsorption groove 104 is evacuated to fix the analytical chip 110 to the substrate 100 by vacuum chuck (step 213).

The four pumps 101-i are driven to fill the four flow paths of substrate 102-i and the four flow paths of analytical chip 112-i, respectively, communicating therewith, with a fluid. As the fluid used, any fluid such as water, an alcohol or air may be used so long as it does not lower the activity of the dNTPs when brought into contact with the dNTPs (step 214).

Then, 5 μL of the DNA sample previously prepared is poured into the reaction cell 113 from above (step 215).

Figure 9:
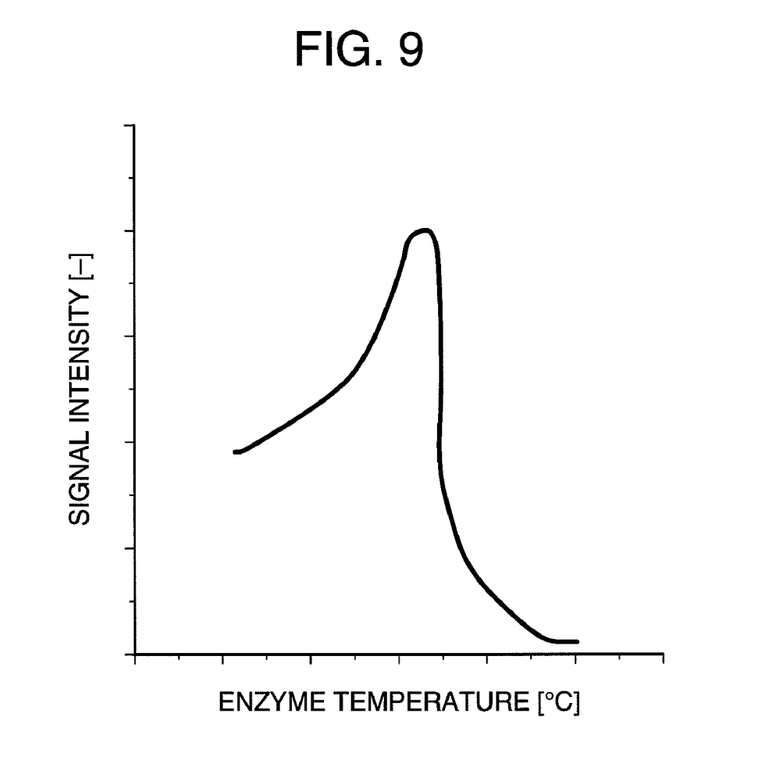
FIG. 9 is a graph showing the effect of temperature control on the amount of light emitted.

Subsequently, the temperature control mechanism 103 is driven to raise the temperature of the DNA sample in the reaction cell 113 in a short time through the base plate 106 of the analytical chip. Several enzymes are contained in the DNA sample and their activity is increased with a rise of the temperature. However, when the enzymes are allowed to stand above a certain temperature for a long period of time, they are denatured to lose their activity rapidly. Therefore, in the reaction of ATP with luciferin in the presence of luciferase (formula (3)), i.e., a final and typical reaction in DNA analysis, temperature control was carried out which consisted of heating the enzymes to each of various preset temperatures in a short time, detecting fluorescence and then cooling the enzymes to room temperature rapidly. FIG. 9 shows the results obtained. When the enzymes were heated to 43° C. in a short time, the amount of light emitted became twice that attained at 20° C. That is, by raising the temperature of the DNA sample to about 43° C. in a short time, the amount of light emitted which is detected in the analysis can be increased to twice that attained at 20° C. The amount of light emitted is sufficiently increased also when the enzymes are heated to 40° C. An amount of light emitted which is larger than that attained at 200C can be attained by heating the enzymes to 25° C. or higher.

Since the amount of light emitted is thus increased by raising the temperature of the DNA sample in a short time, the value of a luminous signal is increased as compared with background noises, so that the emitted light can be detected with high sensitivity (step 216). The temperature of the DNA sample is raised by at least 5° C. in view of, for example, the activity of the enzymes. The temperature is raised to at most 45° C. from the same viewpoint.

Then, one of the four pumps 101-i, for example, the pump 101-1 is driven to send 0.1 μL of a fluid filling up the flow path of substrate 102-1 and the flow path of analytical chip 112-1. By this sending, 0.1 μL of dATP is introduced into the reaction cell 113 from the dATP vessel 111-1 connected to the flow path of analytical chip 112-1, through the dATP nozzle 114-1 (step 217).

When the dATP introduced binds to the DNA sample, light is emitted within 1 second. Therefore, the combination of the DNA sample with the dATP can be detected by measuring the emitted light with a photodetector 120 (step 218).

Thereafter, the temperature inside the reaction cell 113 is lowered to room temperature in a short time by operating the temperature control mechanism 103. This is because the decomposition of the unbound dATP by the mixed reagent requires about 50 seconds and hence the enzymes lose their activity if the temperature inside the reaction cell 113 is maintained at 43° C. during the decomposition (step 219).

The base sequence of the DNA sample 201 is analyzed by carrying out the same operations as above for each of dCTP 212, dTTP 213 and dGTP 214. That is, the temperature inside the reaction cell 113 is raised to 43° C. in a short time by operating the temperature control mechanism 103 (step 220).

Then, 0.1 μL of dCTP is introduced into the reaction cell 113 from the dCTP vessel 111-2 through the dCTP nozzle 114-2 by driving the pump 101-2 (step 221).

The combination of the DNA sample with the dCTP is detected by measuring emitted light with a photodetector 120 (step 222).

Thereafter, the temperature inside the reaction cell 113 is lowered to room temperature in a short time by operating the temperature control mechanism 103 during the decomposition of the unreacted dCTP by the mixed reagent (step 223).

The temperature inside the reaction cell 113 is raised to 43° C. in a short time by operating the temperature control mechanism 103 again (step 224).

Then, 0.1 μL of dTTP is introduced into the reaction cell 113 from the dTTP vessel 111-3 through the dTTP nozzle 114-3 by driving the pump 101-3 (step 225).

The combination of the DNA sample with the dTTP is detected by measuring emitted light with a photodetector 120 (step 226).

Thereafter, the temperature inside the reaction cell 113 is lowered to room temperature in a short time by operating the temperature control mechanism 103 during the decomposition of the unreacted dTTP by the mixed reagent (step 227).

Lastly, the temperature inside the reaction cell 113 is raised to 43° C. in a short time by operating the temperature control mechanism 103 again (step 228).

Then, 0.1 μL of dGTP is introduced into the reaction cell 113 from the dGTP vessel 111-4 through the dGTP nozzle 114-4 by driving the pump 101-4 (step 229).

The combination of the DNA sample with the dGTP is detected by measuring emitted light with a photodetector 120 (step 230).

Thereafter, the temperature inside the reaction cell 113 is lowered to room temperature in a short time by operating the temperature control mechanism 103 during the decomposition of the unreacted dGTP by the mixed reagent (step 231).

The above process is repeated for the four kinds of dNTPs to determine the base sequence of the DNA sample, base by base (step 232).

Since there is a possibility of combination of dATP with dTTP or combination of dCTP with dGTP, the dNTPs are preferably reacted in such an order that dATP and dTTP, or dCTP and dGTP, do not succeed one another as described above. By employing this order, contamination of the dNTPs with one another can be prevented, so that each dNTP can be certainly tried to be combined with the DNA sample.

Figure 10:
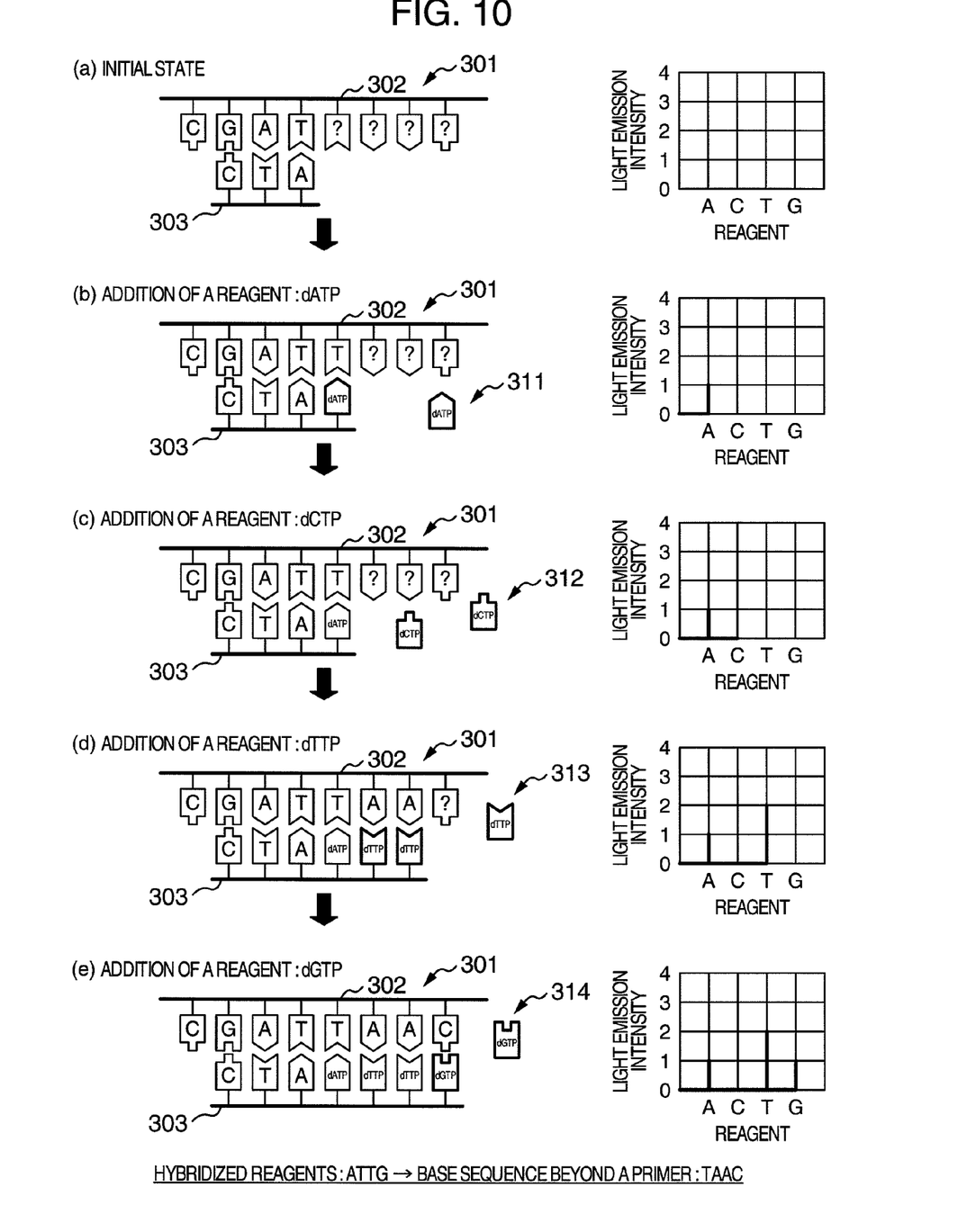
FIG. 10 is a schematic view illustrating the combinations of a DNA sample with a dNTP.

Actual combination of the DNA sample with the dNTPs in the case of analyzing the base sequence of the DNA sample according to the above procedure is explained with reference to FIG. 10. FIG. 10 is a schematic view showing the combination of the DNA sample with the dNTPs.

A DNA sample 301 is composed of a single-stranded DNA sample 302 and a primer 303 bonded to the single-stranded DNA sample 302. As shown in FIG. 10(a), the initial state of the DNA sample 301 is that in the case where the primer 303 is bonded to the single-stranded DNA sample 302 and the base sequence beyond the primer 303 of the single-stranded DNA sample 302 is unknown. The symbols used for expressing the base sequence are as follows; A: adenine, G: guanine, C: cytosine, and T: thymine.

When dATP 311 is added to the DNA sample 301 in the above-mentioned initial state in the presence of the mixed reagent, dATP 311 is bonded to the DNA sample 301 as shown in FIG. 10(b). By detecting light emitted in this case, a change in the amount of light emitted is measured which corresponds to a single base. Thereafter, the unreacted dATP 311 is decomposed with the mixed reagent.

When dCTP 312 is then added in the presence of the mixed reagent, dCTP 312 is not bonded to the DNA sample 301 as shown in FIG. 10(c). Therefore, no change in the amount of light emitted is measured by detecting emitted light. Thereafter, the unreacted dCTP 312 is decomposed with the mixed reagent.

When dTTP 313 is then added in the presence of the mixed reagent, two molecules of dTTP 313 are bonded to the DNA sample 301 one after another as shown in FIG. 10(d). By detecting light emitted in this case, a change in the amount of light emitted is measured which corresponds to two bases. Thereafter, the unreacted dTTP 313 is decomposed with the mixed reagent.

When dGTP 314 is lastly added in the presence of the mixed reagent, dGTP 314 is bonded to the DNA sample 301 as shown in FIG. 10(e). By detecting light emitted in this case, a change in the amount of light emitted is measured which corresponds to a single base. Thereafter, the unreacted dGTP 314 is decomposed with the mixed reagent.

The profile of the light emission intensity measured by the above process indicates the order of one base due to dATP 311, two bases due to dTTP 313, and one base due to dGTP 314. Therefore, the base sequence beyond the primer 303 of the single-stranded DNA sample 301 is found to be TAAC by the above analysis.

Although the base sequence of DNA is analyzed in the present example, a wide variety of subjects such as RNA, proteins, allergy, various antigens, etc. can be analyzed.

For example, analysis for the infection of a sample (containing an antigen) with an infectious disease can be carried out by filling the reaction cell of the analytical chip with the sample, introducing a reagent (for example, HBs antibody for the diagnosis of hepatitis B virus disease, or HCV antibody for the diagnosis of hepatitis C virus disease) into the reaction cell from the reagent vessel, and detecting the agglutination of the antigen and the antibody in the reaction cell by means of a photodetector.

In addition, analysis for a protein, enzyme or the like in blood can be carried out by filling the reaction cell with serum, and introducing the reagent for blood analysis disclosed in Japanese Patent Application Kohyo No. 9-504732 into the reaction cell from the reaction vessel, followed by colorimetry with an absorptiometer.

As described above, as compared with a method comprising allowing a sample and a reagent to flow down along a flow path while mixing them in the flow path, and detecting their reaction in 3 to 5 minutes, the present invention makes it possible to detect the reaction of a sample with a reagent in a short time (for example, about 1 second) by batchwise mixing of the sample and the reagent in the reaction cell 113 having a very small capacity of 5 μL. Moreover, according to the present invention, a small and portable analyzer can be provided which requires no large laser for excitation and is obtained merely by placing the analytical chip 110 on the substrate 100 and combining the simple photodetector 120 therewith. Furthermore, optimum circumstances for POC examination can be created by providing a user with the disposable analytical chip 110 in which reagents have been previously stored in amounts required for only one run of examination and which is in a frozen state.

Example 2

Figure 11:
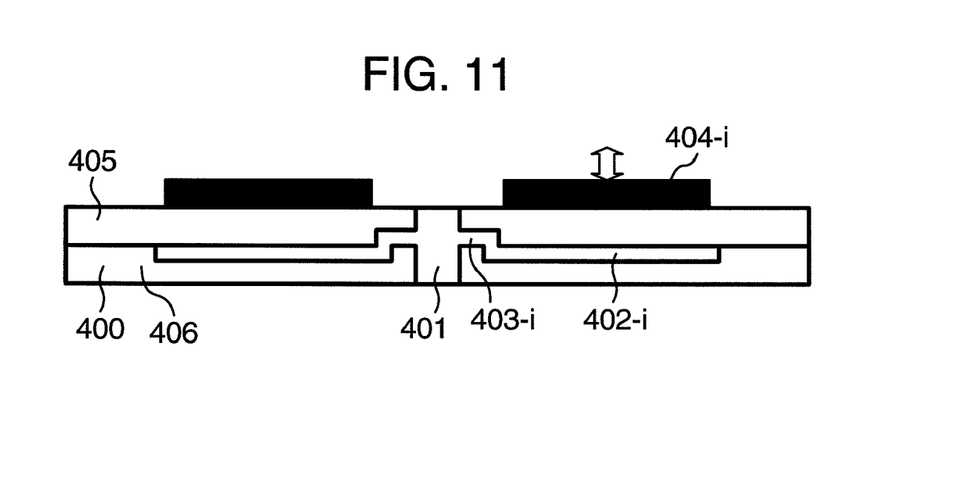
FIG. 11 is a cross-sectional view showing the structure of the analytical chip shown in FIG. 2.

Although in Example 1, the reagents are sent by the use of the pumps 101-i because the reagents are individually introduced into the reaction cell 113 many times, the analysis can be easily carried out by utilizing the change in capacity of the reagent vessels shown in FIG. 11, when the reagents are individually introduced once or twice. That is, a reaction cell 401, reagent vessels 402-i and reagent nozzles 403-i are provided in an analytical chip 400. Actuators 404-i are located over the reagent vessels 402-i, respectively. In the production of the analytical chip 400, reagents are previously introduced into the reagent vessels before joining a PDMS first layer 405 having the reaction cell 401 and reagent nozzles 403-i formed therein according to a pattern, to a PDMS second layer 406 having the reaction cell 401 and reagent vessels 402-i formed therein according to another pattern, and just after joining the two PDMS layer, the resulting analytical chip 400 is quickly frozen, whereby the reagents can be enclosed in the reagent vessels 402-$i$ without being decreased in activity.

The reagents are individually introduced into the reaction cell 401 by depressing the reagent vessels 402-$i$ downward by driving the actuators 404-$i$, respectively, located over the reagent vessels 402-$i$. Since PDMS is a soft material, the reagent vessels 402-$i$ can be deformed when the thickness of the PDMS first layer 405 is 0.1 to 1 mm.

Although such an analytical chip is somewhat inferior to that described in Example 1 in the precision of introduction of the reagents, an analyzer can be miniaturized because a pump for vacuum exhaustion required for fixing the analytical chip to a substrate by vacuum chuck and pumps for sending the reagents are unnecessary.

Example 3

Figure 12:
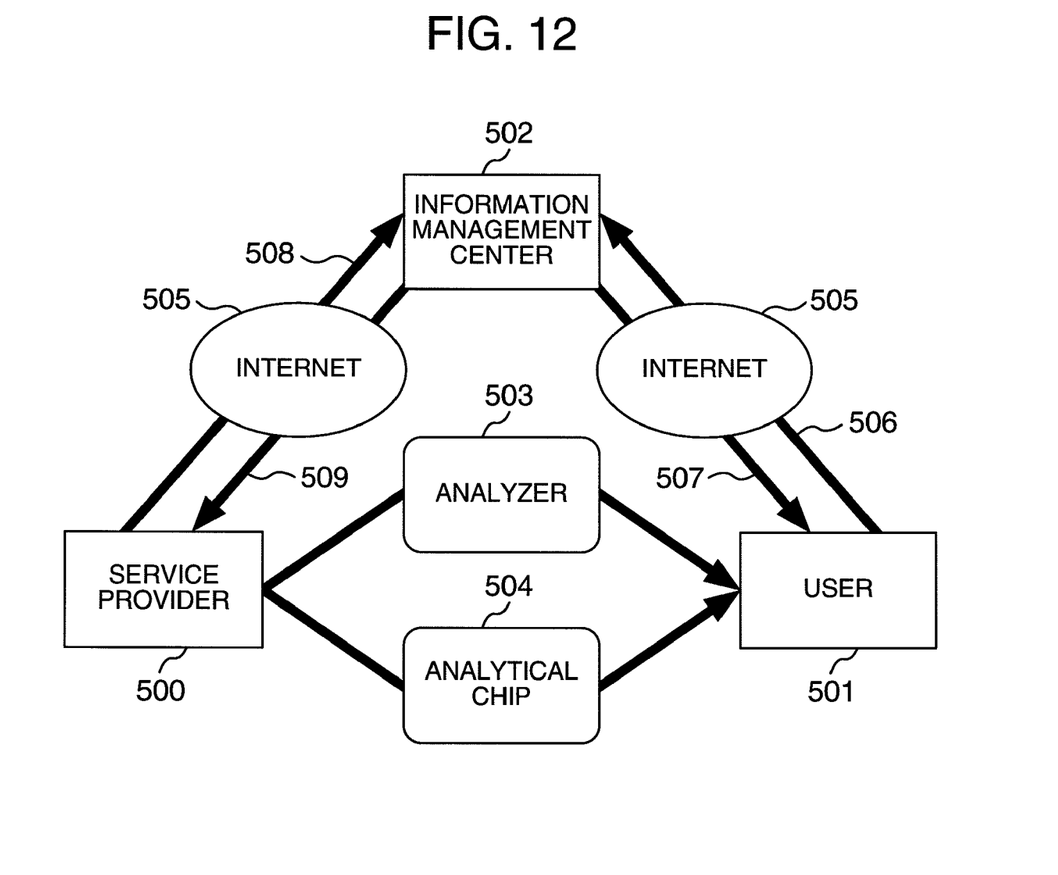
FIG. 12 is an illustration showing POC examination service using the analytical chip of the present invention as an essential.

FIG. 12 shows a service for POC (Point-of Care) using the analytical chip and analyzer of the present invention. A service provider 500 provides a user 501 with an analyzer 503 suitable for POC and a disposable analytical chip 504 to be set in the analyzer 503. In this case, the analytical chip 504 is in a frozen state. The user 501 can exchange data with an information management center 502 through an internet 505. That is, the user 501 has access to the information management center 502 to register user ID. The user 501 transmits examination data 506 together with the user ID to the information management center 502 after examination, whereby the user 501 can obtain diagnosis information 507 based on the examination data 505 from the information management center 502. On the other hand, the information management center 502 and the service provider 500 exchange data with each other through the internet 505. That is, the information management center 502 transmits consumption data 509 concerning the analytical chip 504 consumed by the user 501 and the user ID to the service provider 500 in exchange for a database 508 including genetic analysis information and clinical data, which the information management center 502 receives from the service provider 500. After receiving the above information transmitted, the service provider 500 can prepare reagents suitable for use situation for each user 501 and can provide the user 501 rapidly with the analytical chip 504 in which these reagents have been stored in a frozen state. The user 501 can receive the analytical chip 504 having the prepared reagents instantly stored therein in a frozen state, and hence can carry out examination without spending his or her labor for maintaining the activity of the reagents.

A specific example of the case where the information management center 502 has a database is described below.

The user 501 transmits analysis result information such as the examination data 506 and the previously registered ID of the user 501 to the information management center 502. The ID is that certified, for example, by the user and the information management center. The information management center 502 transmits the diagnosis information 507, i.e., evaluation information obtained by evaluation based on information in said database which corresponds to the examination data 506 received, to the user 501. The examination data 506 is incorporated into the database and utilized for higher-precision diagnoses. Transmitting equipment may be installed for the above transmission. Receiving equipment may be installed for the reception. Controlling equipment may be installed for the incorporation.

Thus, the information management center 502 can construct a database consisting of many data samples, by providing evaluation of the examination data 506 transmitted which is based on the original database. Therefore, the information management center 502 can carry out higher-precision evaluation. Particularly when a subject for analysis is such that the tendency of a disease can be apprehended by accumulation of information on a sample as in the case of a genetic sequence, etc., the precision can be effectively improved.

The above-mentioned analysis regarding genes may be, for example, analysis regarding a genetic sequence in a specific site. The database concerning genetic information may be a database concerning a disease due to a genetic sequence in a specific site. The evaluation described above may be, for example, the rate of onset of a disease such as cancer which is determined based on genetic polymorphism information.

The analysis described above can be carried out as not only analysis regarding genes but also analysis regarding other items on a sample. In the analysis regarding other items, the aforesaid database concerning genetic information is replaced with a database concerning, for example, the degree of allergy of an individual subjected to the analysis and the intensity of the adverse effects of a drug.

In addition, the information management center 502 receives information on use of an apparatus for the above analysis from the user 501. This use information preferably includes, for example, information on consumption of the expendable supplies of the apparatus. Owing to this information, the information management center 502 can know the degree of consumption of the expendable supplies of the apparatus for the analysis and the like and hence can provide the user 501 with effective services.

The aforesaid information management center receives the information on use of the apparatus, such as the consumption data and transmits this use information to the service provider 500 which utilizes said use information. The service provider 500 provides the information management center with a genetic and clinic database 508.

Owing to the above previous information exchange between the information management center 502 and the aforesaid specific service provider 500, the information management center 502 can increase information accumulated in its database effectively and hence can carry out high-precision evaluation.

Owing to the above previous information exchange between the service provider 500 and the aforesaid specific information management center 502, the service provider 500 can collect the information on use of the apparatus by the user and hence can provide effective services.

When preparations for examination services for POC are thus made by using the disposable analytical chip 504 as an essential, the user 501 can obtain the diagnosis information 507 while saving time and labor, and the analytical chip 504 is rapidly supplied.

It should be further understood by those skilled in the art that the foregoing description has been made on embodiments of the invention and that various changes and modifications may be made in the invention without departing from the spirit of the invention and the scope of the appended claims.

What is claimed is:

1. An analyzer comprising a reaction cell into which a sample collected from a living body is introduced and four reagent storage portions in which reagents to be supplied to said reaction cell are stored, for carrying out a DNA sequencing by supplying said reagents to said reaction cell and optically detecting the reaction, which further comprises:

an analytical chip which is made of a resin, comprising said reaction cell, said four reagent storage portions containing dATP, dCTP, dTTP and dGTP, respectively, four reagent nozzle portions constituting a four flow paths which connect each of said four reagent storage portions to said reaction cell, and four analytical chip flow paths which are connected to each of said four reagent storage portions;

a pump for vacuum exhaustion;

a substrate including an analytical chip setting portion having a suction groove, wherein said analytical chip is set and fixed by suction by evacuating said suction groove with said pump for vacuum exhaustion;

four substrate flow paths of said substrate which communicate with each of said four analytical chip flow paths, when said analytical chip is set in said substrate;

four pumps which are connected to each of said four substrate flow paths, for discharging a fluid which does not lower an activity of said reagents;

a temperature control mechanism for raising or lowering a temperature of said reaction cell when said analytical chip is set in said analytical chip setting portion; and an optical detector which is located to face said reaction cell, when said analytical chip is set in said substrate, wherein:

said analytical chip is set and fixed by suction in said substrate, and said four substrate flow paths and said four analytical chip flow paths communicating therewith are filled with said fluid by driving said four pumps, a process which comprises introducing said four reagents from said reagent storage portions into said reaction cell through said four reagent nozzle portions after said sample is introduced into said reaction cell, by driving one of said four pumps and sending said fluid from said four analytical chip flow paths to said four reagent storage portions, and measuring emitted light with said optical detector, is repeated, said four reagents in said four reagent storage portions have been stored in amounts required for one run of examination, said analytical chip has been preserved in a frozen state and is thawed to carry out a DNA sequencing, and the reagent nozzle portion connecting each reagent storage portion to a reaction cell includes a region where the sectional area is 15,000 $\mu m^2$ or less.

2. The analyzer according to claim 1, wherein a the temperature control mechanism raises a temperature of said reaction cell after said reagents are introduced into said reaction cell, and a DNA analysis is carried out with said optical detector.

3. The analyzer according to claim 1, wherein the reagents are sequentially introduced into the reaction cell in the following order: dATP, dCTP, dTTP and dGTP.

* * * * *